(12) United States Patent
Freyman et al.

(10) Patent No.: US 7,332,160 B2
(45) Date of Patent: Feb. 19, 2008

(54) MEDICAL DEVICE AND METHOD FOR TISSUE REMOVAL AND REPAIR

(75) Inventors: Toby Freyman, Watertown, MA (US); Wendy Naimark, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 680 days.

(21) Appl. No.: 10/194,762

(22) Filed: Jul. 12, 2002

(65) Prior Publication Data

US 2004/0010306 A1   Jan. 15, 2004

(51) Int. Cl.
*A61K 38/48* (2006.01)
*A61K 9/64* (2006.01)
*A61K 9/58* (2006.01)
*A61K 9/50* (2006.01)
*A61F 13/00* (2006.01)
*A61F 2/00* (2006.01)
*C12N 11/08* (2006.01)

(52) U.S. Cl. ............... 424/94.63; 424/422; 424/426; 424/460; 424/462; 424/490; 435/180; 435/213; 435/219

(58) Field of Classification Search ............ 424/94.63, 424/422, 426, 447, 460, 462, 490; 435/173, 435/180, 213, 219, 325
See application file for complete search history.

(56) References Cited

U.S. PATENT DOCUMENTS

| | | | | |
|---|---|---|---|---|
| 5,827,531 A | * | 10/1998 | Morrison et al. | 424/450 |
| 5,863,957 A | * | 1/1999 | Li et al. | 521/61 |
| 6,280,411 B1 | * | 8/2001 | Lennox | 604/103.05 |
| 6,348,042 B1 | * | 2/2002 | Warren, Jr. | 604/8 |
| 6,458,386 B1 | * | 10/2002 | Schacht et al. | 424/488 |
| 6,703,040 B2 | * | 3/2004 | Katsarava et al. | 424/444 |
| 6,759,431 B2 | * | 7/2004 | Hunter et al. | 514/449 |
| 2001/0006630 A1 | | 7/2001 | Yacoby-Zeevi | |
| 2002/0099438 A1 | * | 7/2002 | Furst | 623/1.16 |
| 2003/0021775 A1 | * | 1/2003 | Freeman | 424/94.63 |
| 2003/0022856 A1 | | 1/2003 | Richardson et al. | |

FOREIGN PATENT DOCUMENTS

| | | | |
|---|---|---|---|
| SU | 1111739 A | * | 9/1984 |
| WO | WO 9203172 A1 | * | 3/1992 |
| WO | WO 01/70290 A2 | | 8/2001 |
| WO | WO 01/72280 A2 | | 10/2001 |
| WO | WO 01/72281 A2 | | 10/2001 |

OTHER PUBLICATIONS

English language translation of SU 1111739 A, pp. 1-3.*
NLM website www.nlm.nih.gov/cgi/2006/MB_cgi.*

* cited by examiner

*Primary Examiner*—Sandra E. Saucier
*Assistant Examiner*—Susan Hanley
(74) *Attorney, Agent, or Firm*—Jones Day

(57) ABSTRACT

The present invention relates to medical devices that are to be implanted or inserted into the body of a patient for the purpose of removing undesired body tissues. In one embodiment of the invention the medical device comprises a body tissue removal agent for removing undesired body tissue simultaneously with or prior to treatment of body tissue that is in proximity to the undesired body tissue with a biologically active material. Such biologically active material may facilitate regeneration of the body tissue that was removed or may prevent the recurrence of the undesired body tissue.

12 Claims, 7 Drawing Sheets

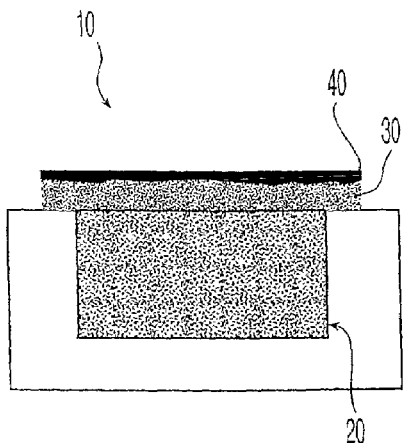
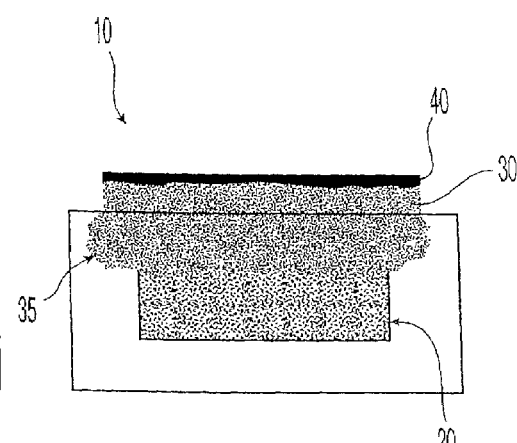
Fig. 1A  Fig. 1B
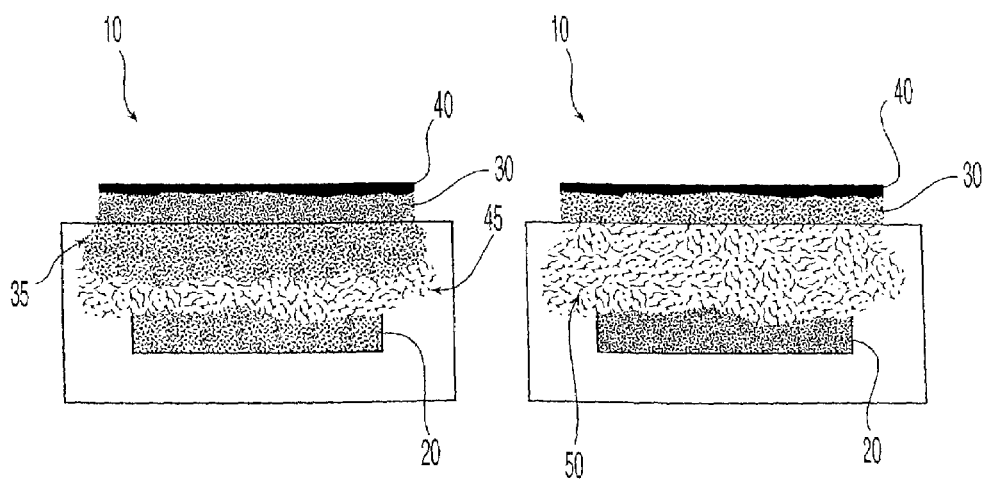
Fig. 1C  Fig. 1D

MEDICAL DEVICE AND METHOD FOR TISSUE REMOVAL AND REPAIR

FIELD OF THE INVENTION

The present invention relates to medical devices and methods for removing undesired body tissue from a patient. More particularly, the present invention relates to implantable or insertable medical devices and methods for removing damaged, injured or unwanted body tissue prior to, or simultaneously with, the application of a biologically active material to body tissue that is in proximity to the undesired body tissue.

BACKGROUND OF THE INVENTION

The interest in using of cells and other biologically active materials, such as therapeutics, to facilitate tissue regeneration has grown significantly. However, in some cases the removal of undesired body tissue, such as diseased or injured tissue, must precede this treatment. A typical method of removing injured or diseased tissue is to surgically excise that tissue. Surgical excision, however, does not adequately address the problem of encouraging new tissue to regenerate in place of the removed tissue. In certain cases, a gradual process of tissue removal and regeneration may be preferred over simply cutting the undesired body tissue away. For example, to minimize acute trauma, such a gradual process may be preferred in removing diseased brain tissue. In another example, surgically excising diseased cardiac tissue may be more traumatic than gradually removing the diseased cardiac tissue for replacement with new cardiac tissue.

Also, surgical removal of tissue and organ parts is not always the best treatment modality, because certain body tissues and organs are difficult to access. Certain body parts, for example, skin and certain organs such as liver are easily accessible during surgery. Surgically excising liver is a viable solution to removing as well as regenerating new tissue because the liver is one of the few body organs which will grow back spontaneously. Brain tissue, however, is not easily accessible, nor does it grow back spontaneously. Cardiac tissue is also difficult to surgically excise and treat without undue trauma because, normally, the heart is continuously beating. In addition, cardiac tissue does not regenerate on its own.

There is a need, therefore, to provide an alternative device and method that removes undesired body tissue, i.e., injured, diseased or unwanted body tissue, yet reduce acute surgical trauma and improve treatment accessibility to certain body tissues and organs. Moreover, there is a need for a device and method for achieving a gradual removal of injured and diseased tissue and furthermore, providing a means for facilitating, either concurrently or subsequently, other forms of treatment therapy on the body tissue in proximity to the undesired body tissue, for example, regeneration of the body tissue or preventing the proliferation of body tissue.

SUMMARY OF THE INVENTION

One embodiment of the present invention provides a medical device for removing undesired body tissue of a patient, e.g., injured or diseased tissue, prior to or simultaneously with treating body tissue in proximity to the undesired body tissue. The medical device comprises a body tissue removal agent for facilitating the removal of the undesired body tissue, and a biologically active material. Also, the medical device can comprise a biodegradable portion which comprises the body tissue removal agent, which may include collagenase, dispase, trypsin, papain, acetic acid and cells that mediate the removal of the undesired body tissue.

In another embodiment of the present invention, the medical device is a stent comprising a sidewall and a coating disposed upon the sidewall. The coating can comprise an outer layer comprising the body tissue removal agent and an inner layer comprising a biologically active material.

Moreover, another embodiment of the medical device of the present invention is a an expandable balloon comprising a coating disposed thereon. Moreover, the coating on the balloon can comprise an outer layer comprising the body tissue removal agent and an inner layer comprising a biologically active material.

In yet another embodiment of the invention, the medical device is a microsphere. The microsphere can comprise an outer portion which contains the body tissue removal agent and an inner portion which contains a biologically active material.

Furthermore, another aspect of the invention provides a patch that is attachable near or at the undesired body tissue. The patch comprises a scaffold material a body tissue removal agent and a biologically active material. The scaffold material can be selected from polylactic acids (PLA), polyglycolic acid (PGA), PLGA, collagen, fibrin, alginate and submucosal tissue. Furthermore, the patch may comprise a first layer that comprises the body tissue removal agent and a second layer that comprises the biologically active material.

A further embodiment of the present invention is a method for removing undesired body tissue of a patient prior to or simultaneously with the treating of body tissue that is in proximity to the undesired body tissue, the method comprising: providing a medical device comprising a body tissue removal agent and a biologically active material; applying the body tissue removal agent to the undesired body tissue; and applying a biologically active material to the body tissue in proximity to the undesired body tissue simultaneously with or after the application of the body tissue removal agent.

BRIEF DESCRIPTION OF THE DRAWINGS

The present invention will be explained with reference to the following drawings:

FIGS. 1a-1d, show cross-sectional views of one embodiment (a patch) of the present invention showing the sequence of the removal of undesired body tissue or tissue degradation and new tissue formation of body tissue;

DETAILED DESCRIPTION OF THE INVENTION

Figure 2:
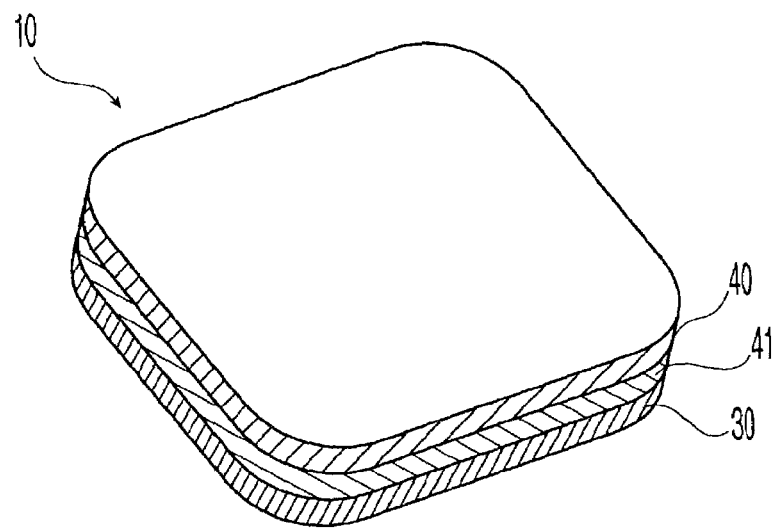
FIG. 2 shows a perspective view of a bi-layered patch implant, in accordance with the present invention, with an optional separation membrane.

The present invention provides a medical device and method for facilitating the removal of undesired body tissue such as diseased or injured tissue or other unwanted body material. The device may be placed at or near the site of the undesired body tissue. In accordance with the present invention, the body tissue removal agent may be integrated into the medical device or it can be controllably delivered to the undesired body tissue. The body tissue removal agent facilitates the removal of the undesired body tissue by directly causing the degradation of the undesired body tissue or causing other cells to scavenge the undesired body tissue.

In another aspect of the present invention, a biologically active material may be incorporated into the medical device to treat body tissue that is near or in contact with the undesired body tissue. The biologically active material may be delivered simultaneously with the body tissue removal agent or subsequent to the delivery of the body tissue removal agent. Alternatively, the biologically active material need not be part of the medical device and may be applied after the body tissue removal agent is applied to the undesired body tissue. The biologically active material is preferably delivered to body tissue that is in proximity to or relatively near the undesired body tissue that is removed or was in contact with the undesired body tissue. The biologically active material preferably facilitates the regeneration of body tissue to replace the removed undesired body tissue.

Suitable medical devices for the present invention include, without limitation, stents, patches, surgical staples, catheters such as central venous catheters, arterial catheters, endocardial injection catheters, and endolumenal infusion catheters, guidewires, balloons, filters (e.g., vena cava filters), cannulas, cardiac pacemaker leads or lead tips, cardiac defibrillator leads or lead tips, implantable vascular access ports, stent grafts, vascular grafts or other grafts, interluminal paving system, intra-aortic balloon pumps, heart valves, cardiovascular sutures, total artificial hearts, ventricular assist pumps, and GDC coils.

The medical devices suitable for the present invention may be fabricated from polymeric and/or metallic materials. Examples of such polymeric materials include polyurethane and its copolymers, silicone and its copolymers, ethylene vinyl-acetate, poly(ethylene terephthalate), thermoplastic elastomer, polyvinyl chloride, polyolephines, cellulosics, polyamides, polyesters, polysulfones, polytetrafluoroethylenes, acrylonitrile butadiene styrene copolymers, acrylics, polylactic acid, polyclycolic acid, polycaprolactone, polyacetal, poly(lactic acid), polylactic acid-polyethylene oxide copolymers, polycarbonate cellulose, biological polymers (in general) and compolymers including collagen and PEO, genetically engineered protein polymers, and chitins. Examples of suitable metallic materials include metals and alloys based on titanium (e.g., nitinol, nickel titanium alloys, thermo-memory alloy materials), stainless steel, platinum, tantalum, nickel-chrome, certain cobalt alloys including cobalt-chromium-nickel alloys (e.g., Elgiloy® and Phynox®) and gold/platinum alloy. Metallic materials also include clad composite filaments, such as those disclosed in WO 94/16646.

The body tissue removal agents that are suitable for the present invention include, but are not limited to enzymes that promote degradation of injured or diseased tissue. These enzymes include: collagenase, dispase, trypsin, papain, and metalloproteases. Other body tissue removal agents are chemicals which act directly on the tissue to cause degradation, for example, acetic acid, ethanol, phenol, hydrogen peroxide, and surfactants such as lipids, stearates, and PEG. Still other body tissue removal agents are cells that either remove or stimulate the removal of diseased tissue. Such cells include, without limitation, monocytes, macrophages, fibroblasts, osteoclasts, foreign body giant cells, and genetically engineered versions with enhanced degradative properties. These cells also include, without limitation, SP (side population cells), Lin$^-$ (lineage negative cells), Lin$^-$CD34$^-$, Lin$^-$CD34$^+$, Lin$^-$cKit$^+$, MSC (mesenchymal stem cells), cord blood cells, cardiac or other tissue-derived stem cells, whole bone marrow, BM-MNCs (bone marrow mononuclear cells), EPCs (endothelial progenitor cells), skeletal myoblasts, MDCs (muscle derived cells), go cells, endothelial cells, and adult cardiomyocytes. The adult cardiomyocytes include, without limitation, MSCs+5-aza, adult cardiac fibroblasts+5-aza, genetically modified cells, MyoD scar fibroblasts, embryonic stem cell clones, embryonic stem cells, sertolic cells, MSCs, cord blood cells, fetal or neonatal cells, MSCs+5-aza, immunologically masked cells, genetically modified cells, and teratoma derived cells. Other body tissue removal agents are growth factors that recruit white blood cells such as monocytes and macrophages that scavenge dead or injured cells. Examples of suitable growth factors include gamma intereron, lymphotoxin, interluken 4, interluken 1, IFN-gamma, IFN-alpha, IFN-beta, interluken 3, M-CSF, GM-CSF, and TNF-alpha.

Examples of biologically active materials suitable for the present invention include therapeutics such as pharmaceuticals as well as cells and genetic materials and proteins. A particular suitable therapeutic agent is G-SCF (granulocyte-colony stimulating factor) which increases the concentration of stem cells in the peripheral blood.

The genetic materials mean DNA or RNA, including, without limitation, of DNA/RNA encoding a useful protein stated below, anti-sense DNA/RNA, intended to be inserted into a human body including viral vectors and non-viral vectors. Examples of DNA suitable for the present invention include DNA encoding transcription factor P31/27 tRNA interference sequences (RNAc's)

anti-sense RNA tRNA or rRNA to replace defective or deficient endogenous molecules angiogenic factors including growth factors, such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor cell cycle inhibitors including CD inhibitors thymidine kinase ("TK") and other agents useful for interfering with cell proliferation such as EZF decoys, and the family of bone morphogenic proteins ("BMP's") as explained below. Viral vectors include adenoviruses, gutted adenoviruses, adeno-associated virus, retroviruses, alpha virus (Semliki Forest, Sindbis, etc.), lentiviruses, herpes simplex virus, ex vivo modified cells (e.g., stem cells, fibroblasts, myoblasts, satellite cells, pericytes, cardiomyocytes, sketetal myocytes, macrophage), replication competent viruses (e.g., ONYX-015), and hybrid vectors. Non-viral vectors include artificial chromosomes and mini-chromosomes, plasmid DNA vectors (e.g., pCOR), cationic polymers (e.g., polyethyleneimine, polyethyleneimine (PEI)) graft copolymers (e.g., polyether-PEI and polyethylene oxide-PEI), neutral polymers PVP, SP1017 (SUPRATEK), lipids or lipoplexes, nanoparticles and microparticles with and without targeting sequences such as the protein transduction domain (PTD).

The biological materials include cells, yeasts, bacteria, proteins, peptides, cytokines and hormones. Examples for peptides and proteins include growth factors (FGF, FGF-1, FGF-2, VEGF, Endotherial Mitogenic Growth Factors, IGF, and epidermal growth factors, transforming growth factor α and β, platelet derived endothelial growth factor, platelet derived growth factor, tumor necrosis factor α, hepatocyte growth factor and insulin like growth factor), transcription factors, proteinkinases, CD inhibitors, thymidine kinase, serine protease inhibitors (including SERP-1), and bone morphogenic proteins (BMP's), such as BMP-2, BMP-3, BMP-4, BMP-5, BMP-6 (Vgr-1), BMP-7 (OP-1), BMP-8. BMP-9, BMP-10, BMP-11, BMP-12, BMP-13, BMP-14, BMP-15, and BMP-16. Currently preferred BMP's are BMP-2, BMP-3, BMP-4, BMP-5, BMP-6, BMP-7. Alternatively or in addition, molecules capable of inducing an upstream or downstream effect of a BMP can be provided. Such molecules include any of the "hedgehog" proteins, or the DNA's encoding them. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include whole bone marrow, bone marrow derived mono-nuclear cells, progenitor cells (e.g., endothelial progenitor cells) stem cells (e.g., mesenchymal, hematopoietic, neuronal), pluripotent stem cells, fibroblasts, macrophage, and satellite cells. These cells also include, without limitation, SP (side population cells), $Lin^-$ (lineage negative cells), $Lin^-CD34^-$, $Lin^-CD34^+$, $Lin^-cKit^+$, MSC (mesenchymal stem cells), cord blood cells, cardiac or other tissue-derived stem cells, whole bone marrow, BM-MNCs (bone marrow mononuclear cells), EPCs (endothelial progenitor cells), skeletal myoblasts, MDCs (muscle derived cells), go cells, endothelial cells, and adult cardiomyocytes. The adult cardiomyocytes include, without limitation, MSCs+5-aza, adult cardiac fibroblasts+5-aza, genetically modified cells, MyoD scar fibroblasts, embryonic stem cell clones, embryonic stem cells, MSCs, cord blood cells, fetal or neonatal cells, MSCs+5-aza, immunologically masked cells, genetically modified cells, teratoma derived cells, and matrix metalloproteases (MMPs).

Among the cells that may be particularly suitable for the invention are stems cells for cell seeding. The technology for cell seeding tissue to promote tissue regeneration is well known in the art. Other therapeutic agents include growth factors which encourage growth of new tissues by stimulating cell activity such as secretion of enzymes and phagocytosis. In addition, other agents may facilitate removal of old tissue by recruiting or stimulating the development of macrophages, monocytes, fibroblasts, osteoclasts and foreign body giant cells to the treatment area. Another example of therapeutic agent is processed submucosal tissue refined by CorMatrix, Inc. Submucosal tissue has the ability to facilitate tissue repair without being modified or requiring the inclusion of other therapeutics. Therefore, in addition to being a biodegradable scaffold it can serve as a therapeutic as well. In particular, cells migrate to and infiltrate such scaffold, and then the cells proliferate and resorb back into the scaffold, forming new healthy tissue. Submucosal tissue may be used in conjunction with other therapeutic agents.

Biologically active material also includes non-genetic therapeutic agents, such as:

anti-thrombogenic agents such as heparin, heparin derivatives, urokinase, and PPack (dextrophenylalanine proline arginine chloromethylketone);

anti-proliferative agents such as enoxaprin, angiopeptin, or monoclonal antibodies capable of blocking smooth muscle cell proliferation, hirudin, and acetylsalicylic acid, amlodipine and doxazosin;

anti-inflammatory agents such as glucocorticoids, betamethasone, dexamethasone, prednisolone, corticosterone, budesonide, estrogen, sulfasalazine, and mesalamine;

immunosuppressants such as sirolimus (RAPAMYCIN), tacrolimus, everolimus and dexamethasone, antineoplastic/antiproliferative/anti-miotic agents such as paclitaxel, 5-fluorouracil, cisplatin, vinblastine, vincristine, epothilones, methotrexate, azathioprine, halofuginone, adriamycin, actinomycin and mutamycin; endostatin, angiostatin and thymidine kinase inhibitors, and its analogs or derivatives;

anesthetic agents such as lidocaine, bupivacaine, and ropivacaine;

anti-coagulants such as D-Phe-Pro-Arg chloromethyl keton, an RGD peptide-containing compound, heparin, antithrombin compounds, platelet receptor antagonists, anti-thrombin anticodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors and tick antiplatelet peptides;

vascular cell growth promotors such as growth factors, Vascular Endothelial Growth Factors (FEGF, all types including VEGF-2), growth factor receptors, transcriptional activators, and translational promotors;

vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;

cholesterol-lowering agents; vasodilating agents; and agents which interfere with endogenous vasoactive mechanisms;

anti-oxidants, such as probucol;

antibiotic agents, such as penicillin, cefoxitin, oxacillin, tobranycin angiogenic substances, such as acidic and basic fibrobrast growth factors, estrogen including estradiol (E2), estriol (E3) and 17-Beta Estradiol; and drugs for heart failure, such as digoxin, beta-blockers, angiotensin-converting enzyme (ACE) inhibitors including captopril and enalopril.

Also, the biologically active materials of the present invention include nitric oxide adducts, which prevent and/or treat adverse effects associated with use of a medical device in a patient, such as restenosis and damaged blood vessel surface. Typical nitric oxide adducts include nitroglycerin, sodium nitroprusside, S-nitroso-proteins, S-nitroso-thiols, long carbon-chain lipophilic S-nitrosothiols, S-nitrosodithiols, iron-nitrosyl compounds, thionitrates, thionitrites, sydnonimines, furoxans, organic nitrates, and nitrosated amino acids, preferably mono-or poly-nitrosylated proteins, particularly polynitrosated albumin or polymers or aggregates thereof. The albumin is preferably human or bovine, including humanized bovine serum albumin. Such nitric oxide adducts are disclosed in U.S. Pat. No. 6,087,479 to Stamler et al. which is incorporated herein by reference.

Moreover, a biologically active material may be encapsulated in micro-capsules by the known methods.

The following provides a description of preferred embodiments in accordance with the present invention. In one of these embodiments, the medical device comprises a patch. Examples of patches that are implanted or inserted into the patient for treatment are described in U.S. Pat. Nos. 6,171,344; 6,096,347; and 4,947,840. There a number of manufacturing methods for making patches. For example, such methods include, but are not limited to, lyophilization of a proteinaceous slurry, isolation of tissue from mammals, salt leeching polymeric materials, protein gel formation, and synthetic or natural polymer forming processes.

The shape or configuration of the patch is determined by the particular body tissue being treated and its location in the body. The patch is comprised of a scaffold material and a body tissue removal agent that is released from the patch. The scaffold material is preferably biodegradable. Examples of suitable scaffold materials may be selected from the following materials: polylactic acids (PLA), polyglycolic acid (PGA), polygluconate (PLGA), collagen, fibrin, alginate and gel foam or a combination of these materials. In addition, submucosal tissue may be used as a biodegradable scaffold material.

The body tissue removal agent may be incorporated into the patch by applying such agent to the scaffolding material as a coating. Such coating may be in the form of a gel, puddy, foam, or paste so that the body tissue removal agent is applied to the undesired body tissue through a diffusion process. Alternatively, the body tissue removal agent may be infused into or dispersed within the scaffold material. Preferably, the portion of the patch containing the body tissue removal agent is placed in direct contact with the undesired body tissue. In addition, a biologically active material for the regeneration of body tissue to replace the undesired body tissue may be incorporated into the patch by coating the scaffold material or infusing or dispersing such material into the scaffold material.

FIGS. 1(a)-1(d) depict an example of a patch of the present invention. This patch 10 is comprised of two layers of a scaffold material 30 and 40. The patch 10 can be attached to the body tissue to be treated 20. The patch 10 is comprised of a first or inner layer 30 which can contain the body tissue removal agent, for example, an enzyme. The patch 10 is also comprised of a second or outer layer 40 which can contain the biologically active material. FIG. 1(a) shows the attachment of the patch 10 such that the inner layer 30 is in contact with the tissue to be treated 20. The inner layer 30 can be loaded with a body tissue removal enzyme which is slowly released into the undesired body tissue 20 until that tissue is degraded and removed by natural body processes. FIG. 1(b) shows the dispersal of a body tissue removal enzyme 35 (body tissue removal agent) into the undesired body tissue 20. The enzyme becomes depleted as it is consumed by natural body processes. The space in the body tissue that is created upon removal of the undesired body tissue 45 should be filled by new body tissue cells generated from the body tissue in proximity to the undesired body tissue 45 or from the circulatory system. The second or outer layer 40 of the patch 10 can deliver a biologically active material, such as stem cells, for facilitating the regeneration of the removed undesired body tissue. FIG. 1(c) shows the space created by the removal of the undesired body tissue being filled with body fluids, cells and a biologically active material from the outer layer 40. FIG. 1(d) shows newly forming cells 50 that fill the space.

The total thickness of the patch 10 may vary between about 100 microns to about 1 cm, depending on the application. For a patch used for cardiac applications, the total patch thickness should be preferably about 1 to 5 millimeters. If cells are used either as a body tissue removal agent or as a biologically active material, the scaffold material of the patch should have pores which are sized between about 1 to 200 microns. The volume of the pores in the scaffold material should preferably be greater than 50% and more preferably greater than 90% of the total volume of the scaffold material.

Additionally, if cells are used as either the body tissue removal agent or the biologically active material and are infused or dispersed in the scaffold material, the scaffold material should preferably allow sufficient nutrients to reach the cells while they remain within the scaffold material. In order to allow the cells to receive sufficient nutrients, microchannels can be created within the scaffold material to permit nutrients to reach the cells within the scaffold material.

As shown in FIG. 2, in another embodiment of the patch, the first or inner layer 30 and the second or outer layer 40 may be optionally separated by a biodegradable membrane layer 41, such that when the body tissue removal agent is consumed and the undesired body tissue is removed, the membrane layer is then degraded, allowing for the time-release of the biologically active material contained in the outer layer 40. In particular, by selecting the material used to make the separation membrane 41 and/or designing the thickness or configuration of the separation membrane 41, such membrane can be degraded over a period of time wherein the undesired body tissue is completely removed before the biologically active material is released. One of skill in the art is aware of how to select the separation membrane materials as well as their thicknesses and configurations to achieve the desired degradation rate of the separation membrane. Other examples of suitable materials for the membrane include, but are not limited to, polyester, collagen, fibrin, polylactic acid, polyglycolic acid, PLGA, PEG-PLGA, polycarbonate, and polytyrosine polymers.

Figure 3:
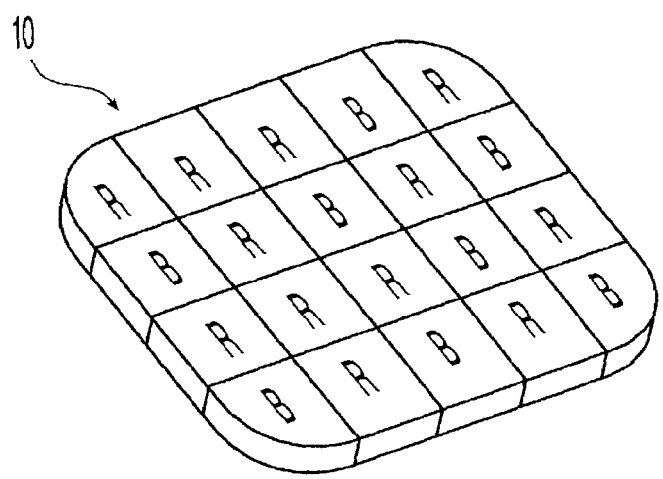
FIG. 3 shows a perspective view of a patch implant, in accordance with the present invention, with one possible arrangement for containing and dispensing a body tissue removal agent (R) and a biologically active material (B)
Figure 4:
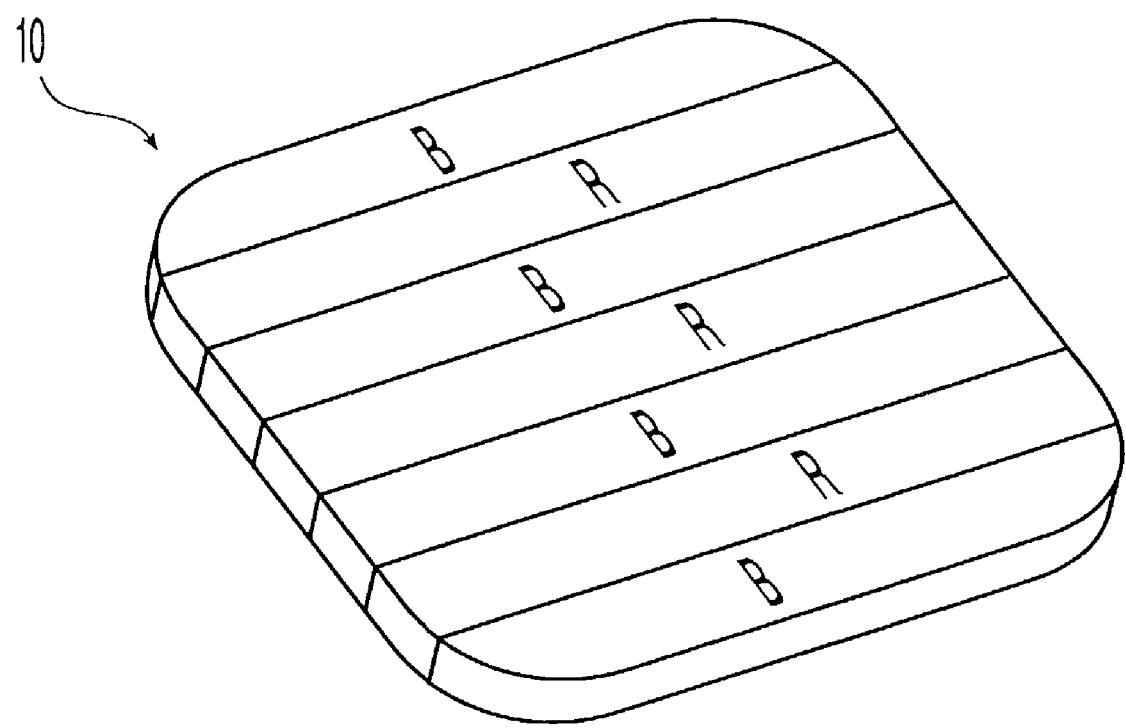
FIG. 4 shows a perspective view of a patch implant, in accordance with the present invention, with another possible arrangement for containing and dispensing a body tissue removal agent (R) and a biologically active material (B)
Figure 5:
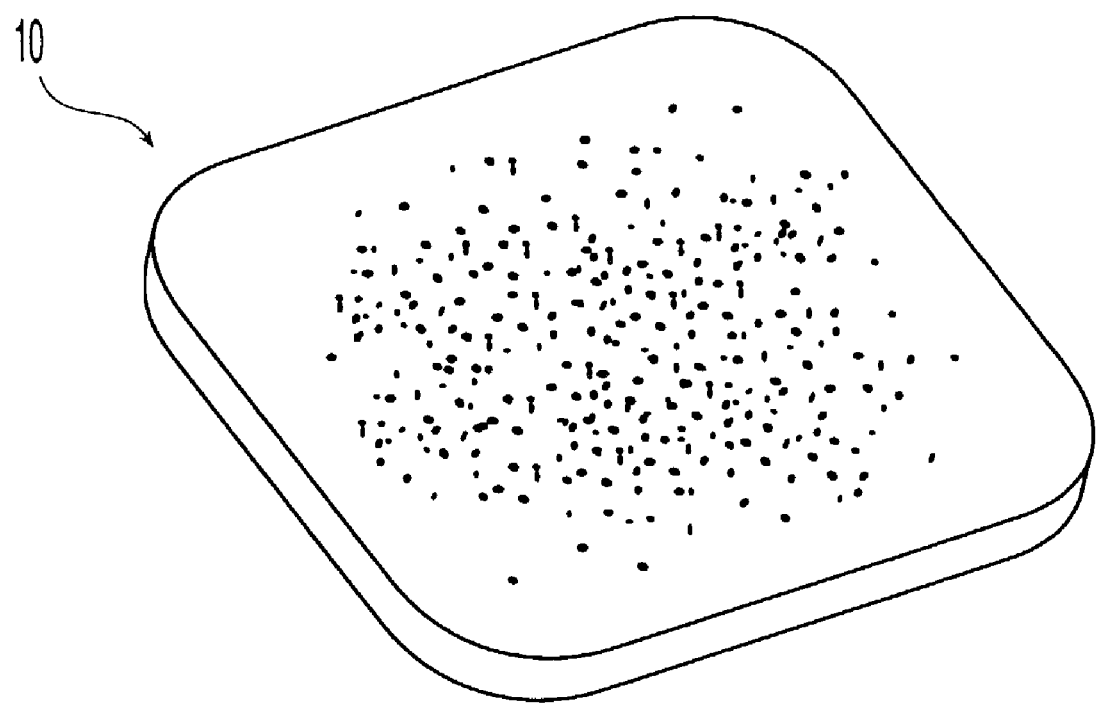
FIG. 5 shows a perspective view of a patch implant, in accordance with the present invention, showing how the body tissue removal agent or biologically active material may be loaded in the patch with a higher concentration of the agent and/or material in desired locations in the patch.

FIGS. 3-5, depict examples of patches that spatially control the removal of the undesired body tissue. As shown these examples, the body tissue removal agent is not uniformly incorporated in the patch. Therefore, when these patches are applied to undesired body tissue not all of the undesired body tissue will necessarily be removed at the same time. For example as shown in FIG. 3, the patch may be comprised of a checkboard-like pattern of portions that contain only the body tissue removal agent (R) and other portions containing only the biologically active material (B). When the patch is applied to the undesired body tissue, those parts of such tissue that directly contact the portions of the patch that contain the body tissue removal agent will likely be removed faster than the parts of the tissue not in contact with the portions containing the body tissue removal agent. Similarly, as shown in FIG. 4, the patch may comprise of alternating parallel strips that contain only the body tissue removal agent (R) and other strips that only contain the biologically active material (B). When such a patch is applied to the undesired body tissue, those parts of this tissue that directly contact the strips of the patch that contain the body tissue removal agent will likely be removed faster than the parts of the tissue not in contact with the strips containing the body tissue removal agent. It should be noted that the portions or strips containing the body tissue removal agents may be designed to release such agents simultaneously with or in a timed sequence with the biologically active material. Preferably, the body tissue removal agent is applied to the undesired body tissue simultaneously or prior to the application of the biologically active material. The examples discussed above are only a few of the possible arrangements of how the body tissue removal agent and the biologically active material can be incorporated into the patch.

In addition, concentration gradients of the body tissue removal agents and/or the biologically active material can be incorporated into the patch. For instance, if there is a particular part of the undesired body tissue that would be expected to require more body tissue removal agent than other parts, that particular part should be placed in contact with the portion of the patch that has a higher concentration of the body tissue removal agent. On the other hand, the portions of the patch containing lesser concentrations can be applied to those parts of the undesired body tissue that need less of the body tissue removal agent. The gradient in the patch may be located in the plane of the patch (i.e., along the face of the patch) as shown in FIG. 5 where there is more body tissue removal agent and/or biologically active material located at the center of the patch and less of the agent or material near the edges of the patch. Alternatively, the gradient may be locate out of the plane of the patch (i.e., varying along the thickness of the patch). Thus, concentrations gradients may be incorporated into the patch in order to direct the delivery of the body tissue removal agent and/or the biologically active material to a particular point or area of the tissue to be treated.

Other than spatially controlling the removal of the undesired body tissue and/or the treatment of the body tissue in proximity to such undesired body tissue, such removal and/or treatment can be controlled temporally. For instance, the concentration of the biologically active material can be increased to prolong the duration in which the biologically active material is released. Also, the release rate of the body tissue removal agent or the biologically active material can be adjusted by varying the particle sizes of such agents or materials. Furthermore, such release rate may be adjusted by adjusting the pore size of the scaffold material containing the agent and/or material.

The patch can be delivered to the undesired body tissue by means that are known to the skilled artisan, such as a catheter. The patch can be affixed to the undesired body tissue or body tissue in proximity thereto in a number of ways. For example, the patch could be sutured to the body tissue or attached using a medical adhesive. The sutures and medical adhesive may be biodegradable. If there are a number of areas that need treatment or the area to be treated is larger than the area covered by a single patch, multiple patches can be used.

Figure 6A:
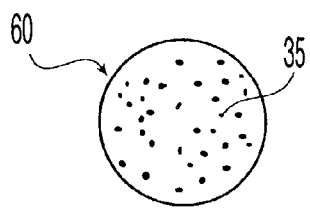
FIG. 6a shows, in accordance with the present invention, a cross-sectional view of a biodegradable, injectable microsphere loaded with a body tissue removal agent.
Figure 6B:
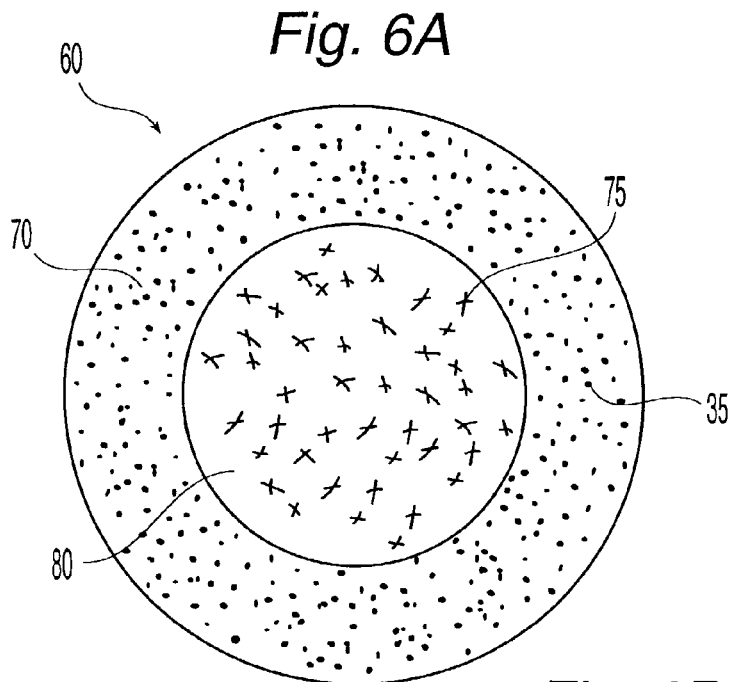
FIG. 6b shows, in accordance with the present invention, a cross-sectional view of a biodegradable microsphere which has an outer portion and an inner portion, wherein the outer portion contains a body tissue removal agent and the inner portion contains a biologically active material agent.
Figure 6C:
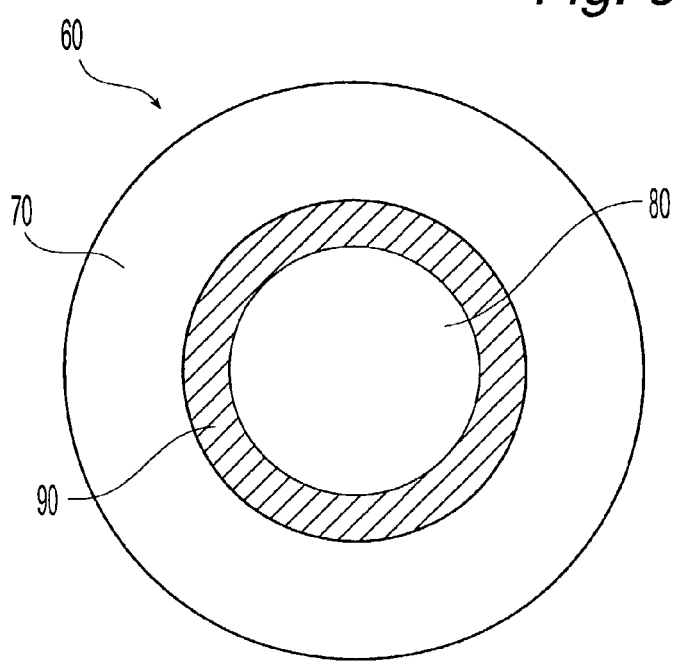
FIG. 6c shows, in accordance with the present invention, a cross-sectional view of a biodegradable microsphere of FIG. 6b, but with the addition of a separation membrane between the outer portion and inner portion.

Yet another embodiment of the medical device in accordance with the present invention is microspheres as shown in FIGS. 6a-c. For a description of a standard emulsion technique for preparing microspheres, see, e.g., Bhagat, H. R. et al., "A novel, self-correcting membrane coating technique." Pharm. Res., 8(5):576-83, May 1991; and Pekarek, K. J., et al., "Double-walled polymer microspheres for controlled drug release." Nature, 367(6460):258-260, Jan. 20, 1994. As shown in FIG. 6a, one embodiment of the microsphere 60 contains only a body tissue removal agent 35. As shown in FIGS. 6b and 6c, another embodiment of the invention provides microspheres with a layered structure comprising at least two-layers, an outer portion 70 which can contain a body tissue removal agent 35 and an inner portion or core 80 which can contain a biologically active material 75.

In operation, these microspheres 60 can be injected into a site of diseased or injured tissue, particularly those body sites which may be difficult to access with a surgeon's scalpel and which would experience acute tissue trauma. For example, using a long, flexible needle, microspheres may be injected into remote brain tissue or a beating heart. Once the microspheres are delivered to the desired location in the patient, the body tissue removal agent 35 can be gradually consumed and the undesired body tissue can thereby be removed. After sufficient time has passed to allow removal of the undesired body tissue, the inner portion or core 80 of the microsphere will be exposed to body tissue and the biologically active material can be released or applied to body tissue in proximity to the removed undesired body tissue. Also, as shown in FIG. 6c, in one embodiment of the layered micosphere, the outer layer 70 and inner layer or core 80 may be separated by a biodegradable membrane 90 having time-dependent degradation properties. The composition of the membrane 90 may be designed to achieve time-dependent release of the biologically active material.

Figure 7A:
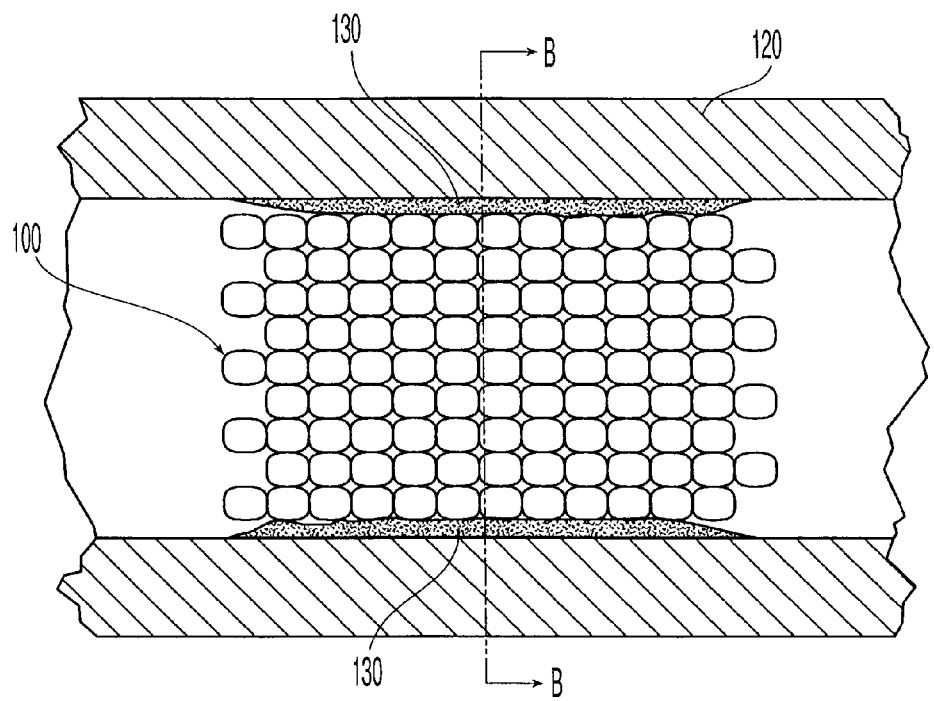
FIG. 7a shows a longitudinal, cross-sectional view of a body lumen with plaque and a longitudinal, side view of a stent implant, in accordance with the present invention.
Figure 7B:
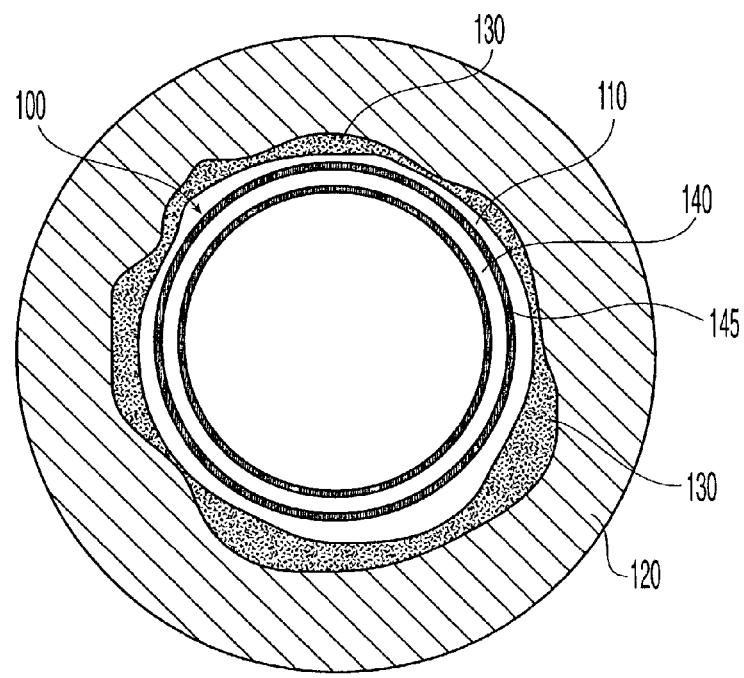
FIG. 7b shows a cross-sectional view of the stent implant and body lumen shown in FIG. 7a at line B-B.

FIG. 7a depicts another embodiment of the present invention. In this embodiment, the medical device is a stent 100 having a sidewall and a coating on the sidewall. The coating comprising the body tissue removal agent. The coating preferably comprises a biodegradable material which contains the body tissue removal agent. Such a stent 100 may be used to treat plaque formation 130 in a body lumen such as a blood vessel 120 and, additionally, to prevent recurrence of the plaque in the same location of the vessel. FIG. 7b provides a cross-sectional view of the stent 100 inside the blood vessel 120 across line B-B of FIG. 7a.

As shown in FIG. 7b, the coating can also, but is not required to comprise a biologically active material. The coating shown in FIGS. 7a and 7b comprises two layers, an outer layer 110 and an inner layer 140. The outer coating layer 110 of the stent 100 contains the body tissue removal agent and the inner coating layer 140 contains a biologically active material. An optional separation membrane 145 may also be provided between the outer and inner layers. This separation membrane can be designed to degrade over time to allow timed-release of the biologically active material contained in inner coating layer 140. The outer layer 110 can contain a body tissue removal agent specifically for degrading the plaque 130 or a thrombotic lesion in the vessel wall 120. The inner layer 140 of the coating can contain a biologically active material that can prevent the restenosis of the vessel by preventing plaque or thrombus from recurring or treating restenosis. Suitable biologically active materials for preventing and treating restenosis include without limitation cells, viral and nonviral vectors for delivering gene therapy to the vessel walls anti-thrombotics, anti-proliferatives such as paclitaxel, enoxaprin, heparin, or monoclonal antibodies which block smooth muscle cell proliferation, MMPs, and anti-inflamatory therapeutics such as SERP-1 and IL-10.

In addition to the body tissue removal agent and the biologically active materials, the coating may contain a polymeric material. Examples of suitable polymeric materials for preparing the coating include biodegradable polymeric materials including, but not limited to, polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate, styrene-isobutylene copolymers and blends and copolymers thereof.

In addition to biodegradable polymeric materials, biostable polymeric materials can be used. These biostable material include, but are not limited to, polyurethanes, polyisobutylene and its copolymers, silicones, and polyesters. Other suitable polymers include polyolefins, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate; copolymers of vinyl monomers, copolymers of vinyl monomers and olefins such as ethylene-methyl methacrylate copolymers, acrylonitrile-styrene copolymers, ABS resins, ethylene-vinyl acetate copolymers, polyamides such as Nylon 66 and polycaprolactone, alkyd resins, polycarbonates, polyoxyethylenes, polyimides, polyethers, epoxy resins, polyurethanes, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, and polylactic acid-polyethylene oxide copolymers. Since the polymer is being applied to a part of the medical device which undergoes mechanical challenges, e.g. expansion and contraction, the polymers are preferably selected from elastomeric polymers such as silicones (e.g. polysiloxanes and substituted polysiloxanes), polyurethanes, thermoplastic elastomers, ethylene vinyl acetate copolymers, polyolefin elastomers, and EPDM rubbers.

The coating can be formed on the stent using conventional methods that are known in the art for forming drug-containing coatings. These methods include without limitation spray-coating, dipping the stent with or into a coating formulation containing a polymeric coating material and/or a biologically active material, direct deposition, inkjet coating, and positive displacement.

Figure 8A:
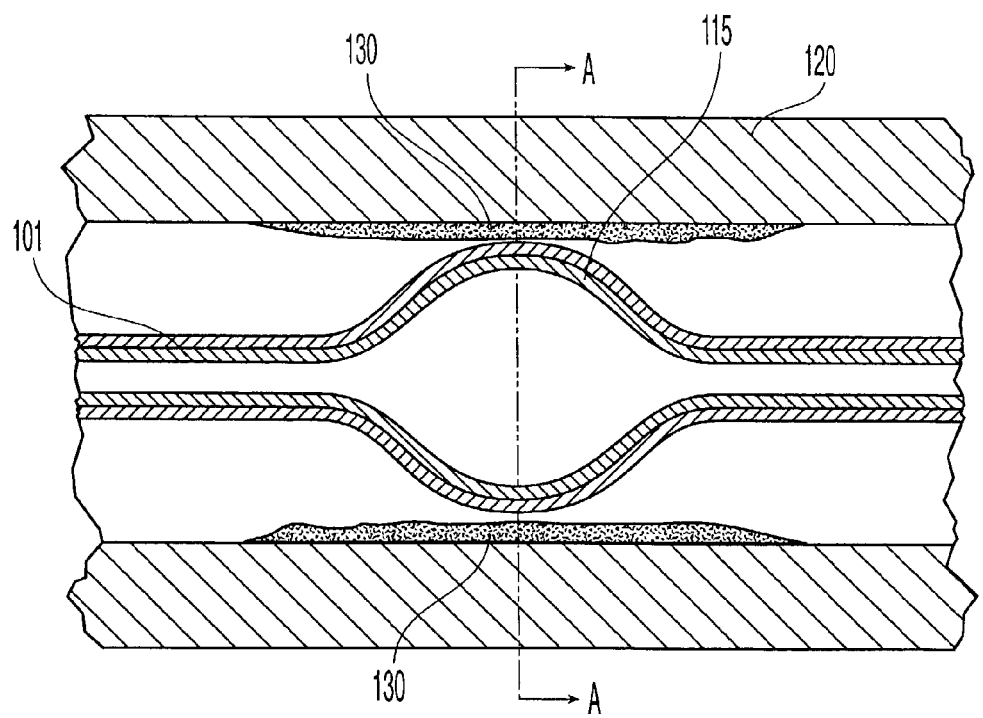
FIG. 8a shows a longitudinal, cross-sectional view of a body lumen with plaque build-up and a longitudinal, cross-sectional view of the balloon implant, in accordance with the present invention.
Figure 8B:
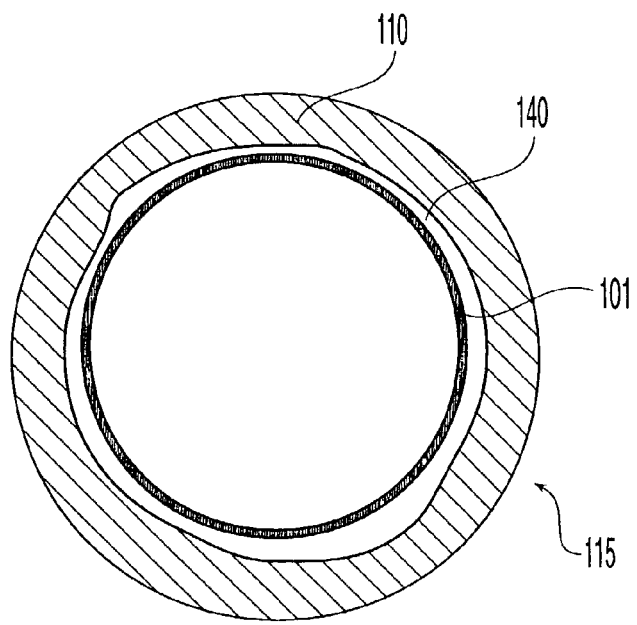
FIG. 8b shows a cross-sectional view of the balloon implant and body lumen shown in FIG. 8a at line A-A.

Moreover, as shown in FIG. 8a, yet another embodiment of the present invention is an expandable balloon 101, such as an endoluminal balloon of a balloon catheter. A coating 115 comprising a body tissue removal agent is applied to the outer surface of the balloon. Such a coating can be formed using conventional methods that are known in the art. FIG. 8b provides a cross-sectional view of the balloon 101 located within a blood vessel 120 across line A-A of FIG. 8a.

As shown in FIG. 8b, the coating 115 can also, but is not required to comprise a biologically active material. Specifically, the coating shown in FIGS. 8a and 8b comprises two layers, an outer layer 110 and an inner layer 140. The outer coating layer 110 of the balloon 101 contains the body tissue removal agent and the inner coating layer 140 contains a biologically active material. The outer layer 110 can contain a body tissue removal agent specifically for degrading the plaque 130 or a thrombotic lesion in the vessel wall 120. While positioned at the targeted site having the plaque 130, the balloon 101 can be dilated causing contact between the balloon coating 110 and the vessel wall 120 and, consequently, allowing the body tissue removal agent to be delivered from the coating to the plaque 130 in the vessel to remove the plaque. The biologically active material of the inner layer 140 is also delivered to the targeted site to prevent or treat restenosis of the vessel. Another exemplary use of this embodiment is the treatment of Barrett's Esophagus. For this condition the balloon delivers an agent which removes cancerous or pre-cancerous cells and/or extracellular matrix proteins. The biologically active material encourages the growth of normal esophageal epithelial cells and extracellular matrix. The biologically active material may include cells or stem cells.

Alternatively, the coating may only contain the body tissue removal agent and not the biologically active material. After the body tissue removal agent is delivered to the undesired body tissue, e.g., plaque, as described above, the biologically active material can be delivered using another balloon or medical device such as a drug coated stent.

It is to be understood that, while various embodiments of the invention have been described, the foregoing are intended only as exemplary embodiments and that other embodiments may be within the spirit and scope of the present invention. It is further understood that other advantages, modifications and embodiments may be within the scope of the present invention as defined by the appended claims.

What is claimed is:

1. A medical device for removing undesired body tissue of a patient prior to or simultaneously with treating body tissue in proximity to the undesired body tissue, wherein the device is a stent comprising a sidewall having a plurality of openings therein, the sidewall having a coating disposed thereon, said coating comprising: (a) an inner layer comprising a biologically active material selected from the group consisting of anti-thrombotics, thrombolytics, anti-proliferative agents, and growth factors; and (b) an outer layer comprising a body tissue removal agent for facilitating the removal of the undesired body tissue prior to or simultaneously with administration of the biologically active material to the body tissue in proximity to the undesired body tissue, wherein the biologically active material and the body tissue removal agent are different.

2. The medical device of claim 1, wherein the medical device comprises a biodegradable polymeric material which comprises the body tissue removal agent.

3. The medical device of claim 1, wherein the body tissue removal agent is selected from the group consisting of collagenase, dispase, trypsin, papain, acetic acid, and cytokines that mediate the removal of the undesired body tissue.

4. The medical device of claim 1, wherein the anti-proliferative agent is paclitaxel.

5. A medical device for removing undesired body tissue of a patient prior to or simultaneously with treating body tissue in proximity to the undesired body tissue, the device comprising an expandable balloon and a coating disposed thereon, wherein the coating comprises: (a) an inner layer comprising a biologically active material selected from the group consisting of anti-thrombotics, thrombolytics, anti-proliferative agents, and growth factors; and (b) an outer layer comprising a body tissue removal agent for facilitating the removal of the undesired body tissue prior to or simultaneously with administration of the biologically active material to the body tissue in proximity to the undesired body tissue, wherein the biologically active material and the body tissue removal agent are different.

6. The medical device of claim 5, wherein the outer layer of the medical device comprises a biodegradable polymeric material which comprises the body tissue removal agent.

7. The medical device of claim 5, wherein the body tissue removal agent is selected from the group consisting of collagenase, dispose, trypsin, papain, acetic acid, and cytokines that mediate the removal of the undesired body tissue.

8. The medical device of claim 5, wherein the anti-proliferative agent is paclitaxel.

9. A medical device for removing undesired body tissue of a patient prior to or simultaneously with treating body tissue in proximity to the undesired body tissue, wherein the device is a microsphere that is injectable into body tissue of the patient comprising: (a) an inner layer which is a core comprising a biologically active material selected from the group consisting of anti-thrombotics, anti-proliferative agents, thrombolytics, and growth factors; and (b) an outer layer comprising a body tissue removal agent for facilitating the removal of the undesired body tissue prior to or simultaneously with administration of the biologically active material to the body tissue in proximity to the undesired body tissue, wherein the biologically active material and the body tissue removal agent are different.

10. The medical device of claim 9, wherein the medical device comprises a biodegradable polymeric material which comprises the body tissue removal agent.

11. The medical device of claim 9, wherein the body tissue removal agent is selected from the group consisting of collagenase, dispase, trypsin, papain, acetic acid, and cytokines that mediate the removal of the undesired body tissue.

12. The medical device of claim 9, wherein the inner and the outer layers are separated by a biodegradable membrane that degrades over time.

* * * * *